United States Patent [19]
Berlowitz-Tarrant et al.

[11] Patent Number: 5,916,557
[45] Date of Patent: Jun. 29, 1999

[54] METHODS OF REPAIRING CONNECTIVE TISSUES

[75] Inventors: Laurence Berlowitz-Tarrant, Harvard, Mass.; Anthony Ratcliffe, New York, N.Y.; Shuichi Mizuno, Brookline, Mass.

[73] Assignees: The Trustees of Columbia University in the City of New York, New York, N.Y.; International Technology Management Associates, Ltd., Harvard, Mass.

[21] Appl. No.: 08/863,610

[22] Filed: May 27, 1997

Related U.S. Application Data

[63] Continuation of application No. 08/385,538, Feb. 8, 1995, abandoned, which is a continuation-in-part of application No. 08/150,478, Nov. 12, 1993, abandoned.

[51] Int. Cl.$^6$ ................................................. A61K 38/46
[52] U.S. Cl. ................ 424/94.5; 424/94.6; 424/94.61; 424/94.62; 424/94.63; 424/94.64; 424/94.65; 424/94.66
[58] Field of Search ............................. 424/94.5, 94.6, 424/94.61, 94.62, 94.63, 94.64, 94.65, 94.66

[56] References Cited

U.S. PATENT DOCUMENTS

| | | | |
|---|---|---|---|
| 4,280,954 | 7/1981 | Yannas et al. | 260/123.7 |
| 4,350,629 | 9/1982 | Yannas et al. | 260/123.7 |
| 4,448,718 | 5/1984 | Yannas et al. | 260/123 |
| 4,458,678 | 7/1984 | Yannas et al. | 128/155 |
| 4,505,266 | 3/1985 | Yannas et al. | 128/1 R |
| 4,553,272 | 11/1985 | Mears | 623/1 |
| 4,696,816 | 9/1987 | Brown | 424/94 |
| 4,787,900 | 11/1988 | Yannas | 623/1 |
| 4,846,835 | 7/1989 | Grande | 623/11 |
| 4,935,497 | 6/1990 | Veis et al. | 530/300 |
| 5,041,138 | 8/1991 | Vacanti et al. | 623/16 |
| 5,116,374 | 5/1992 | Stone | 623/16 |
| 5,158,574 | 10/1992 | Stone | 623/66 |
| 5,206,023 | 4/1993 | Hunziker | 424/423 |
| 5,226,914 | 7/1993 | Caplan et al. | 623/16 |

OTHER PUBLICATIONS

Benjamin et al., "Research Review. Fibrocartilage" *J. Anat.*, vol. 171, pp. 1–15, 1990.

Bertolami et al., "Use of Sodium Hyaluronate in Treating Temporomandibular Joint Disorders: A Randomized, Double–Blind, Placebo–Controlled Clinical Trial," *J. Oral Maxillofac. Surg.*, vol. 51, pp. 232–242, 1993.

Craig et al., "A Role for Hyaluronan in Joint Development" *J. Anat.*, vol. 171, pp. 17–23, 1990.

Daniels et al., "Modulation of chondrogenesis by the cytoskeleton and extracellular matrix" *Journal of Cell Science* vol. 100, pp. 249–254, 1991.

Duke et al., "Studies of Chondrogenesis in Rotating Systems" *Journal of Cellular Biochemistry.*, vol. 51, pp. 274–282, 1993.

Eurell et al., "The Effects of Chondroitinase ABC on the Rabbit Intervertebral Disc" *Clinical Orthopaedics and Related Research.*, No. 256, pp. 238–243, Jul. 1990.

Glowacki et al., "Tissue Response to Bone–Derived Implants" *Bone Grafts & Bone Substitutes,* Chapter 8, pp. 84–92.

Ishiguro et al., "Immunolocation of Atypical Chondroitin Sulfate Chains Reacting with the 3–B–3 Monoclonal Antibodies Following Chymopapain–Induced Injury in the Rabbit" Department of Biochemistry, Anatomy and Internal Medicine (Section of Rheumatology). Rush Medical College at Rush–Presbyterian–St. Luke's Medical Center, Chicago IL 60612.

Kato et al., "Experimental Chemonucleolysis With Chondroitinase ABC" *Clinical Orthopaedics and Related Research,* No. 253, pp. 301–308, Apr. 1990.

Koob et al., "Effects of Chondroitinase–ABC on Proteoglycans and Swelling Properties of Fibrocartilage in Bovine Flexor Tendon" *Journal of Orthopaedic Research,* vol. 7, No. 2, pp. 219–227, 1989.

Labat–Robert et al., "Extracellular matrix" *FEBS,* vol. 268, No. 2, pp. 386–393, Aug. 1990.

Langer et al., "Tissue Engineering" *Science,* vol. 260, pp. 920–926, May 14, 1993.

McDevitt et al., "Ultrastructure and Biochemistry of Meniscal Cartilage" *Clinical Orthopaedics and Related Research,* No. 252, pp. 8–18, Mar. 1990.

Mizuno et al., "A Collagen/DBP Spong eSystem Designed for In Vitro Analysis of Chondroinduction" *Mat. Res. Soc. Symp. Proc.,* vol. 252, pp. 133–140, 1992.

Morris–Kay et al., "Immunohistochemical localisation of chondroitin sulphate proteoglycans and the effects of chondroitinase ABC in 9–to 11–day rat embryos" *Development,* vol. 106, pp. 787–798, 1989.

(List continued on next page.)

*Primary Examiner*—Jean C. Witz
*Attorney, Agent, or Firm*—John P. White; Cooper & Dunham LLP

[57] ABSTRACT

The present invention relates to the use of an ECM-altering enzymatic activity, such as a proteoglycanase or a protease, to stimulate the generation of cartilage tissue by inducing chondrocytes to synthesize new cartilage matrix. It has been discovered that treating chondrocytes with an enzymatic activity that modifies the territorial ECM of the cell, especially cell surface proteoglycans, can in and of itself be sufficient to stimulate cartilage production by the chondrocytes. The subject invention can be employed therapeutically to correct or prevent degeneration of connective tissue. For instance, the present method can be used in the treatment of disorders comprising cartilage such as found in an diarthroidal joint (e.g. articular and interarticular cartilage), as well as in the treatment of tendon and ligamental tissues. Such disorders can range from chronic degeneration brought about by disease, overuse, or trauma, to plastic or reconstructive surgery. Moreover, the subject method may also be applied to both the development and implantation of prosthetic devices.

17 Claims, 1 Drawing Sheet

OTHER PUBLICATIONS

Mow et al., "Cartilage and diarthrodial joints as paradigms for hierarchical materials and structures" *Biomaterials,* vol. 13, No. 2, pp. 67–97, 1992.

Olmarker et al., "Effects of Chondroitinase ABC on ntrathecal and Peripheral Nerve Tissue. An in Vivo Experimental Study on Rabbits" *Spine,* vol. 16, No. 1, pp. 43–45, 1991.

Olmarker et al., "Microvascular Effects of Chondroitinase ABC and Chymopapain. An In Vivo Experimental Study on Hamsters and Rabbits" *Clinical Orthopaedics and Related Research,* No. 257, pp. 274–279, Aug. 1990.

Ratcliffe et al., "The Quantitation of Native Chondroitin Sulfate Epitope in Synovial Fluid Lavages and Articular Cartilage from Canine Experimental Osteoarthritis and Disuse Atrophy" *Arthritis and Rheumatism,* vol. 36, No. 7, pp. 1–9, 1993.

Ratcliffe et al., "Increased concentrations of proteoglycan components in the synovial fluids of patients with acute but not chronic joint disease" *Annals of the Rheumatic Diseases,* vol. 47, pp. 826–832, 1988.

Sampath et al., "In vitro transformation of mesenchymal cells derived from embryonic muscle into cartilage in response to extracellular matrix components of bone" *Proceedings of the National Academy of Sciences,* vol. 81, pp. 3419–3423, 1984.

Wiig et al., "The Early Effect of High Molecular Wieght by Hyaluronan (Hyaluronic Acid) on Anterior Cruciate Ligament Healing: An Experimental Study in Rabbits" *Journal of Orthopaedics Research,* vol. 8, pp. 425–434, 1990.

Williams et al., "repair of Articular Cartilage Injury Following Intra–Articular Chymopapain–Induced Matrix Proteoglycan Loss" *Journal of Orthopaedic Research,* vol. 11, pp. 705–716, 1993.

Yamagata et al., "Regulation of Cell–Substrate Adhesion by Proteoglycans Immobilized on Extracellular Substrates" *The Journal of Biological Chemistry,* vol. 264, No. 14, pp. 8012–8018, 1989.

Miyazaki et al., Japanese Journal of Human Genetics 35(2): 215–221 (1990).

Chandrasekar et al., Matrix 12(1): 1–10 (1992).

Vogel et al., Biochem J 223(3): 587–598 (1984).

Figure 1. Exposure of PG-Lt epitopes on Chondroitinase-treated chondrocytes

METHODS OF REPAIRING CONNECTIVE TISSUES

This application is a continuation of U.S. Ser. No. 08/385,538, filed Feb. 8, 1995, now abandoned, which is a continuation-in-part of U.S. Ser. No. 08/150,478, filed Nov. 12, 1993, now abandoned.

BACKGROUND OF THE INVENTION

Evolution in mammals, reptiles, birds and fish has developed extraordinarily efficient musculoskeletal systems for generating and controlling motion. However, the musculoskeletal system is not only an efficient system for delivering useful mechanical energy and load support, but is also capable of synthesizing, processing and organizing complex macromolecules to fashion tissues and organs for specific mechanical functions. An important subset of organs of the musculoskeletal system are the joints. Many types of joints exist in the body. Freely moving joints (ankle, elbow, hip, knee, shoulder, and those of the fingers, toes and wrist) are known as diarthrodial or synovial joints. The intervertebral joints of the spine are not diarthrodial joints as they are fibrous and do not move freely. They do, however, provide the flexibility required by the spine.

Diarthrodial joints enable local motion and other activities of daily life to take place. They perform their function so well that we are often not even aware of their existence nor the function they provide until injury strikes or arthritis develops. From an engineering point of view, these natural bearings are very uncommon structures. Under healthy conditions, they function nearly frictionless and remain almost entirely wear-resistant manner throughout our lives. Failure of the bearings surfaces of the body (i.e. articular cartilage), as with engineering bearings, means a failure of these bearings to provide their central functions. In biomedical terms, failure of diarthrodial joints leads to arthritis. The most common form being Osteoarthrisis or Osetoarthrothesis. Repair of arthritic joints means orthopedic surgery to replace the worn-out joints by a prosthesis or by a biological graft. This is an enormous medical and economic problem, with more than thirty million Americans suffering from the disabling disease.

Diarthrodial joints have some common structural features. First, all diarthrodial joints are enclosed in a strong fibrous capsule. Second, the inner surfaces of the joint capsule are lined with a metabolically active tissue, the synovium, which secretes the synovial fluid that lubricates the joint and provides the nutrients required by the avascular cartilage. Third, the articulating bone ends in the joint are lined with a thin layer of hydrated soft tissue known as articular cartilage. These linings, i.e. the synovium and articular cartilage layers, form the joint cavity which contains the synovial fluid. Thus, in animal joints, the synovial fluid, articular cartilage, and the supporting bone form the bearing system which provides the smooth nearly-frictionless bearing system of the body. While diarthrodial joints are subjected to an enormous range of loading conditions under cyclical conditions, the cartilage surfaces undergo little wear and tear under normal circumstances. Indeed, most human joints must be capable of functioning effectively under very high loads and stresses and at very low operating speeds. These performance characteristics demand efficient lubrication processes to minimize friction and wear of cartilage in the joint. Sever breakdown of the joint cartilage by either biochemical or biomechanical means leads to arthritis and thus arthritis is defined as a failure of the animal bearing system. Finally, the joint is stabilized by, and in motion is controlled by, ligaments and tendons which may be inside or outside the joint capsule.

Hyaline cartilage, as the names implies is glass smooth, glistening and bluish white in appearance, although older or diseased tissue tends to lose this appearance. The most common hyaline cartilage, and the most studied, is the articular cartilage. This tissue covers the articulating surfaces of long boned and siesamoid bones within diarthrodial joints. Articular cartilage is characterized by a particular structural organization. It consists of specialized cells (chondrocytes) embedded in an intercellular material (typically referred to as "cartilage matrix") which is rich in proteoglycans, collagen fibrils, other proteins, and water. Cartilage tissue is neither innervated nor penetrated by the vascular or lymphatic systems. However, in the mature joint of adults, the underlying subchondral bone tissue—which forms a narrow, continuous plate between the bone tissue and the cartilage—is innervated and vascularized. Beneath this bone plate, the bone tissue forms trabeculae, containing the marrow. In immature joints, articular cartilage is underlined by only primary bone trabeculae. A portion of the meniscal tissue in joints (referred to as the "interarticular" cartilage) also consists of cartilage whose make-up is similar to articular cartilage. It is generally believed that because articular cartilage lacks a vasculature, damaged cartilage tissue does not received sufficient or proper stimuli to elicit a repair response.

The menisci of the knee, and other similar structures such as the disc of the temporomandibular joint and the labrum of the shoulder, are specialized fibrocartilagenous structures which perform functions which are vital for normal joint function. They are known to assist the articular cartilage in distributing loads across the joint, assist the ligaments and tendons in providing joint stability, play a major role in shock absorption, and may assist in lubrication of the joint. Damage to these structures can lead to a reduction in joint function and degeneration of the articular cartilage. Surgical removal can result in early onset of osteoarthritis. The menisci, disc and labrum are hydrated fibrocartilage structures composed primarily of collagen (type I) with smaller amounts of other collagens and proteoglycans (including aggrecan and the smaller, non-aggregating proteoglycans). They contain a sparse population of cells which, like the chondrocytes of cartilage, are responsible for the synthesis and maintenance of this extracellular matrix.

Skeletal ligaments are specialized connective tissues that connect bones. They serve a passive mechanical function in stabilizing joints and in guiding joint motion. Further, they may have a neurosensory role transporting dynamic information to muscles. Ligaments are composed primarily of type I collagen organized in parallel arrays, with small amounts of other collagens, proteoglycans, elastin and other proteins and glycoproteins. The cells are fibroblastic in the midsubstance, and appear more chondroid at and near the insertion sites. Tendons have a similar structure, with a relatively high concentration of collagen, organized primarily as fibers in parallel. Other components are proteoglycans, elastin and other proteins and glycoproteins. The cells are fibroblastic in nature. The cells of the tendon and ligament are metabolically active and are responsible for the synthesis and maintenance of this extracellular matrix.

Proteoglycans comprise the second largest portion of the organic material in articular cartilage. These macromolecules are composed of a protein core to which are attached a number of covalently bound GAG chains (chondroitin sulfate and keratan sulfate). There are many different types of proteoglycans present in a wide range of tissues throughout the body; presumably, they also have different functions in the various tissues. However, the most extensively studied proteoglycans have been those from articular cartilage because of its role in regulating skeletal growth, joint function and the development of arthritis.

The major proteoglycans present in articular cartilage are the large aggregating type (50–85%) and the large non-aggregating type (10–40%) with distinct small proteoglycans also present. The molecular weights of these proteoglycan monomers range from $1 \times 10^6$ to $4 \times 10^6$, and they contribute significantly to the mechanical and physicochemical properties of cartilage. These molecules are highly ordered structures with length scales ranging from $10^{-8}$ to $10^{-6}$ m. First, there is an extended protein core with several distinct regions: an N-terminal region with two globular domains (G1 and G2), a keratan sulfate-rich domain, a longer chondroitin sulfate-rich domain which may also contain some interspersed keratan sulfate and neutral oligosaccharide chains, and a C-terminal globular domain (G3) on the proteoglycan monomer. Aggregates are formed when many proteoglycan monomers bind to a long monofilament chain of hyaluronan via their G1 globular domain. Each proteoglycan-hyaluronan bond is stabilized by a separate globular link protein (mw, 41,000–48,000), and this stabilization is vital in providing additional strength to the molecular network formed by proteoglycans in concentrated solutions. The structure of proteoglycan in cartilage is not uniform. The size of the proteoglycan aggregate depends mainly on the size of the hyaluronate chain and may be as large as $350 \times 10^6$, particularly in fetal cartilage. Differences in chain length and amounts of keratan sulfate and chondroitin sulfate, length of the protein core, and degree of aggregation all contribute to the compositional and structural heterogeneties of proteoglycans within the tissue.

The GAG chains of the proteoglycans provide important physicochemical properties to cartilage. First, chondroitin sulfate (CS: ~mw, 20,000) is composed of repeating disaccharide units of glucuronic acid and N-acetylgalactosamine with a sulfate ($SO_4$) group and a carboxyl (COOH) group per disaccharide. Evidence exists indicating that these CS chains are the main determinants of frictional resistance against inter-stitial fluid flow. Keratan sulfate (KS) consists of repeating disaccharide units of galactose and N-acetylglucosamine, again averaging approximately one $SO_4$ group per disaccharide. Keratan sulfate content of proteoglycans increases with age from zero in fetal cartilage to a maximum in aging cartilage. Both proteoglycan content and size decrease with increasing severity of OA.

In articular cartilage, molecular interactions occur through collagen-collagen covalent cross-link interactions, and proteoglycan-proteoglycan and collagen-proteoglycan non-covalent (electrostatic and mechanical) interactions. The most well-known interactions are the collagen-collagen covalent cross-links. These cross links are important in providing a strong and stiff collagen network. Thus, in the extracellular matrix these two molecular networks (proteoglycan and collagen) must coexist to form a fiber-reinforced composite solid with the collagen network providing the tensile stiffness and strength, and the proteoglycan network providing the compressive stiffness (via the Donnan osmotic pressure, electrostatic repulsion amongst the fixed negative charges and bulk compressive stiffness). The physical interactions between collagen and proteoglycan can arise from two sources: electrostatic and mechanical. First, evidence exists indicating that the negative charge groups on the proteoglycans can interact with the positive charge groups along the collagen fibrils, and hyaluronates of the aggregate do interact with type II, IX and X collagen. Second, evidence of strong frictional interaction between the proteoglycans and the fine collagen network also exists. No covalent bonding exists between collagen fibrils and proteoglycans. In normal cartilaginous tissue, proteoglycans are slowly but continuously turned over, the degraded molecules are released from the cartilage and are replaced by newly synthesized components. It is the coordinate control of synthesis and degradation of the matrix components by the chondrocytes that maintain normal cartilage. In experimental models of joint disease, for example, there is evidence of charges in the rate of biosynthesis and turnover of proteoglycans, which may contribute to cartilage degeneration. This chondrocyte-mediated degeneration leads to the whole cascade of degenerative bone and connective tissue events that results in osteoarthritis, limb immobilization, and other effects requiring surgical intervention.

Over one million surgical procedures in the United States each year involve cartilage replacement. Current therapies include transplantation with allografts (removing healthy cartilage from a donor, and reimplanting into a joint of the recipient), implantation of artificial polymer or metal prostheses, and surgical removal of old or degenerative cartilage and the surgical treatment of underlying bone to stimulate new cartilage formation. This new cartilage is usually a fibrous cartilage significantly inferior to the hyaline cartilage it is replacing. Other surgical procedures of synovial joints involve the replacement of menisci, ligaments and tendons with biological grafts or artificial tissues. Torn or severed menisci, discs of the temporomandibular joint, labrum of the shoulder, tendons and ligaments often undergo surgical repair. Degenerative loss of articular cartilage, for example, at the acetabular/femoral head artoculation, results in heavy loading of the soft tissue, and can require radical surgery.

Surgical procedures account for only a fraction of the treatment of individuals who suffer from disabling diseases resulting from connective tissue damage and degeneration in synovial joint. Alternative treatment includes conservative treatment (e.g., rest and physical therapy), and treatment is largely directed at symptomatic relief through the use of analgesics and nonsteroidal anti-inflammatory drugs.

There are significant limitations with all present approaches. Artificial prostheses have a limited lifetime, and can fail prematurely. Recurrent replacements of prostheses is not an advisable treatment, and, therefore, the relatively young and active patient is often consigned to slow joint degeneration until the use of prosthetic implants becomes a reasonable clinical option. Prostheses rarely replicate the performance of the original tissue. A prosthesis cannot adapt in response to environmental stress as does a biological tissue, nor can it repair itself. Biological allograft material is in limited supply, appropriate size shape and tissue type are difficult to obtain, and has the risk of carrying infectious diseases. Use of autograft material compromises the site used for the source tissue (e.g., using patella tendon to replace anterior cruciate ligament), and can only offer this tissue once. Biological graft tissue rarely, if ever, is able to provide a tissue with the same functional properties as the original tissue.

There appear to be genetic predisposition's to degenerate diseases of the connective tissues that exacerbate the effects of sport and other early injury. Even during pregnancy, there can be generalized stress on cartilage resulting from tropic hormone levels meant for softening of the pubic symphysis, and these can be exacerbated by congenital predisposition and prior injury.

There is therefore a need to offer a process that can stimulate the biological repair of the connective tissue, or stop the degeneration or slow the progression of degeneration of cartilage, menisci, tendons and ligaments.

SUMMARY OF THE INVENTION

The present invention relates to the use of an ECM-altering enzymatic activity, such as a proteoglycanase or a protease, to stimulate the generation of cartilage tissue by inducing chondrocytes to synthesize new cartilage matrix. It has been discovered that treating chondrocytes with an enzymatic activity that modifies the territorial ECM of the cell, especially cell surface proteoglycans, can in and of itself be sufficient to stimulate cartilage production by the chondrocytes. The subject invention can be employed therapeutically to correct or prevent degeneration of connective tissue. For instance, the present method can be used in the treatment of disorders comprising cartilage such as found in an diarthroidal joint (e.g. articular and interarticular cartilage), as well as in the treatment of tendon and ligamental tissues. Such disorders can range from chronic degeneration brought about by disease, overuse, or trauma, to plastic or reconstructive surgery. Moreover, the subject method may also be applied to both the development and implantation of prosthetic devices.

DETAILED DESCRIPTION OF THE INVENTION

Cartilage, ligament, tendon, menisci, disc of tempromanibular joint and labrum of the shoulder are metabolically active connective tissue. They consist of an extracellular matrix (ECM) that contains a population of cells (chondrocytes in hyaline cartilage and the like, and fibrochondrocytes in fibrocartilage, such as meniscal cartilage), wherein the synthesis and maintenance of the tissue are dependent on the appropriate activities of the chondrocytes (or fibrochondrocytes, or other connective tissue cell) associated with it. The metabolic activities involve both anabolic and catabolic events, which include: (a) the synthesis of matrix components, (b) the incorporation and organization of these components into the matrix, and (c) their degradation and loss from the matrix. The chondrocytes are responsible for orchestration of these events, and their appropriate balance results in a maintenance of the cartilage matrix and its biological function. These cells have the capacity to respond to their environment. The effector agents may be soluble mediators (such as growth factors, cytokines, pharmaceutical agents), matrix composition, hydrostatic pressure, and mechanical load. In normal conditions, these responses are designed to maintain a functional matrix. However, some stimulators may result in the cells responding in a manner which degrades the ECM, or in a manner which results in failed repair, and degradation of the ECM occurs.

The present invention relates to the use of an enzymatic activity, such as a chondroitinase, keratanase, hyaluronidase or protease activity, to stimulate production of a connective tissue matrix by the cells within that matrix. By protease activity, we refer specifically to those proteases that do not substantially cleave the collagen matrix. Rather, protease activity refers specifically to those proteases that act only on the proteins of the proteoglycan element of the matrix, and the like.

The present invention arises from the unexpected finding that enzymatically altering the extracellular matrix of a connective tissue cell, particularly of a chondrocyte, has a stimulatory effect on the production of cartilage matrix and other connective tissue matrices by the treated cells. The subject method is applicable in vivo, as for example, in the restoration or remodeling of a connective tissue. This procedure has the potential to slow, stop, or reverse the progression of the degeneration of connective tissue, such as occurs in osteoarthritis, rheumatoid arthritis and other chronic joint disorders. Further, the present method can be used to treat connective tissue which has undergone traumatic injury or excessive wear, or which is the subject of reconstructive/plastic surgery. The subject method is particularly suitable for application in treatments wherein the cartilage generated is to remain unossified. Moreover, the use of the subject method in healing processes can provide correct regeneration of the connective tissue and thereby reduce the amount of fibrotic tissue that might otherwise occur.

Another aspect of the present method involves the use of such ECM-altering enzymatic activities to stimulate production of cartilage in vitro, such as in the generation of prosthetic devices. A great deal of effort has been exerted over the years to facilitated regeneration and repair of bone and cartilage. Several techniques, including cartilage implants and bone implants and grafts for the remedy of many skeletal disorders and chondrodystropies, can be enhanced by use of the present methods and formulations, both during the formation of the prosthetic and after implantation.

It has been discovered that treating chondrocytes with an enzymatic activity that modifies the territorial ECM of the cell, especially cell surface proteoglycans, can in and of itself be sufficient to stimulate cartilage production by the chondrocytes. The present therapeutic methods have a number of advantages over prior techniques used to repair cartilage. In certain embodiments of the subject method, because of the relatively specific targeting of ECM components of the chondrocyte by an enzymatic activity, such as a chondroitinase, and the concomitant activation of these cells, a tighter regulation of the types of cells stimulated during treatment can be achieved. This is in contrast to the use of general mitogenic agents such as growth factors or cytokines which can elicit responses in a broad range of cells, including cells whose activities can be detrimental to cartilage repair. For example, many mitogens have the effect of stimulating osteogenesis in addition to chondrogenesis, and therefore result in induction of bone formation. Thus, it may be advantageous in those circumstances where osteogenic processes are undesirable to treat the tissue in which repair or remodeling of cartilage is desired with a preparation consisting essentially of an ECM-altering enzymatic activity.

The ECM-altering activity useful in the present invention is an enzyme or other catalytic activity which sufficiently alters the extracellular matrix of a chondrocyte, especially the proteoglycans of the territorial matrix of the cell, so as to induce the chondrocytes to synthesize cartilage matrix. In one embodiment, the ECM-altering activity is a proteoglycanase which digests chondroitin sulfate glycosaminoglycan chains of proteoglycans associated with the chondrocytes. Such enzymatic activities can also digest other GAG chains, including dermatan sulfate and hyaluronate. In an illustrative embodiment, the proteoglycanase is a dissacharidase, such as a chondroitin lyase (chondroitinase), which can catalyze the depolymerization of chondroitin sulfate GAGs, particularly chondroitin-6-sulfate and chondroitin-4-sulfate, by the elimination of 1,4 hexosaminidic bonds. For example, chondroitin ABC lyase (EC 4.2.2.4) is a particularly useful chondroitinase activity which catalyzes depolymerization of a glycosaminoglycan containing 1,4-β-D-hexosaminyl and 1,3-β-D-glucuronosyl or 1,3-α-D-iduronosyl linkages by elimination of Δ-4,5-D-glucuronate residues from the glycosaminoglycan. Other proteoglycanase activities useful in the present invention include chondroitin AC lyase (EC 4.2.2.5), Hyaluronoglucosaminidase (EC 3.2.1.35), Hyaluronoglucuronidase (EC 3.2.1.36), β-N-acetylglucosaminidase (EC 3.2.2.30), Hyaluronate lyase (EC 4.2.2.1), Chondroitinsulphatase (EC 3.1.6.4), Chondro-4-sulphatase (EC 3.1.6.9), Chondro-6-sulphatase (EC 3.1.6.10). Further examples of proteoglycanases useful in the subject method can be found, for example, in Endo et al. (1992) *Tanpakushitsu Kakusan Koso* 37:2008–2011; Misevic et al. (1990) *J. Cell Biochem.* 43:307–314; Gharbia et al. (1993) *FEMS Immunol. Med. Microbiol.* 6:139–145; Kresse et al. (1987) *Adv. Enzymol. Relat. Areas Mol. Biol.* 60:127–311; and Conzelmann et al. (1987) *Adv. Enzymol. Relat. Areas Mol. Biol.* 60:89–216.

The present invention further contemplates the use of other hydrolases or lyases, including engineered enzymes and catalytic antibodies, which alter the extracellular matrix of the chondrocytes so as to stimulate these cell to initiate cartilage matrix synthesis. One class of enzymes of use in the subject method are proteases which act to cleave the core protein of chondrocyte-bound proteoglycans. For example, in an illustrative embodiment, the chondrocytes are contacted with a trypsin-like activity able to release cell surface proteoglycans by cleaving the core protein of a proteoglycan, such as aggrecan.

In a preferred embodiment, the ECM-altering activity acts primarily on the proteoglycan matrix and leaves any collagen matrix surrounding the chondrocyte substantially intact. By substantially intact, it is meant that no more than 20% of the collagen matrix in the treatment area is enzymatically altered, and more preferably, no more than 5% is altered, and most preferably, no more than 2%. It can be especially advantageous to avoid use of enzymes which, particularly at high concentration, decrease the tensile strength of the collagen matrix in the treatment area.

Furthermore, the ECM-altering agent can be generated as a chimeric protein comprising an additional moiety that binds a component of the extracellular matrix. Such a chimeric molecule can be useful in circumstances wherein diffusion of the enzyme from a treatment site is undesirable, and will function to such an end by virtue of localizing the chimeric molecule at or proximate a treatment site. A ECM-altering enzyme of this embodiment can be generated as the product of a fusion gene, or by chemical cross-linking.

A number of proteins have been characterized from the extracellular matrix (ECM) of connective tissues that will support the localization of a chimeric ECM-altering agent, such as a chondroitinase-containing chimeric protein, at a target site. One example of a well characterized protein is fibronectin. Fibronectin is a large adhesive glycoprotein with multiple functional domains. Several of these domains have matrix attachment activity. For example, one of these is a single "type-III repeat" which contains a tetrapeptide sequence R-G-D-S (Pierschbacher et al. (1984) *Nature* 309:30–3; and Komblihtt et al. (1985) *EMBO* 4:1755–9). Peptides as small as pentapeptides containing these amino acids are able to support attachment to a cell through binding ECM components (Ruoslahti et al. (1987) *Science* 238:491–497; Pierschbacher et al. (1987) *J. Biol. Chem.* 262:17294–8.; Hynes (1987) *Cell* 48:549–54; and Hynes (1992) *Cell* 69:11–25). In fact, several companies have commercialized products based on this cell attachment sequence for use as reagents in cell culture and various biomaterials applications. See, for example, recent catalogs from Telios Pharmaceutical, BRL, Stratagene, Protein Polymer Technologies etc., as well as U.S. Pat. Nos. 4,517,686; 4,589,881; 4,578,079; 4,614,517; 4,661,111; and 4,792,525. In an illustrative embodiment, an RGDS sequence is added to chondroitin ABC lyase to produce a chondroitinase activity having additional ECM localizing characteristics.

The ECM-altering enzyme, or pharmaceutically acceptable salts thereof, may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredients in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the enzyme, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, the pharmaceutical formulation includes, although not exclusively, solutions or a freeze-dried powder of at least one ECM-altering enzyme in association with one or more pharmaceutically acceptable vehicles or diluents, and contained in buffered media at a suitable pH and isosmotic with physiological fluids. For illustrative purposes only and without being limited by the same, possible composition of formulations which may be prepared in the form of solutions for the treatment of connective tissues with an ECM-altering activity are given in the della Valle U.S. Pat. No. 5,218,094. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of the enzyme in isotonic solutions of the desired volume and include, but not exclusively, the use of buffered saline solutions with phosphate or citrate at suitable concentrations so as to obtain at all times isotonic pharmaceutical preparations of the desired pH, for example, neutral pH.

Methods of introducing the ECM-altering activity at the site of treatment include, but are not limited to, intra-articular, intradermal, intramuscular, intraperitoneal, intravenous, subcutaneous, oral, topical, and intranasal. Methods of introduction may also be provided by rechargable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of the enzymatic agent at a particular target site.

An essential feature of certain embodiments of the implant can be the linear release of the ECM-altering enzyme, which can be achieved through the manipulation of the polymer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials*, ed. by David Williams (MIT Press: Cambridge, Mass., 1990); and the Sabel et al. U.S. Pat. No. 4,883,666. In another embodiment of an implant, a source of cells producing the ECM-altering agent, or a solution of hydrogel matrix containing a purified ECM-altering enzyme, is encapsulated in implantable hollow fibers. Such fibers can be pre-spun and subsequently loaded with both agents (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about a source the enzyme (Lim U.S. Pat. No. 4,391,909; Sefton U.S. Pat. No. 4,353,888; Sugamori et al. (1989) *Trans. Am. Artif Intern. Organs* 35:791–799; Sefton et al. (1987) *Biotehnol. Bioeng.* 29:1135–1143; and Aebischer et al. (1991) *Biomaterials* 12:50–55).

Where the ECM-altering enzyme is a chondroitin ABC lyase, the therapeutically effective amount of the enzyme will typically be in the range of 0.005–200 Units/ml, and, more preferably, in the range of 0.1–20 Units/ml. As used herein with respect to the chondroitinase activity, the term Unit is defined as the quantity of chondroitinase that catalyzes the formation of 1 $\mu$mole of unsaturated disaccharide from chondroitin-6-sulfate per min. at 37° C., pH 8.0.

The present invention makes available effective therapeutic methods and compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a tom ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. It may prevent the onset or exacerbation of degenerative disease if applied early enough after trauma.

In one embodiment of the present invention, the subject method is used therapeutically to generate a cartilage repair response in a connective tissue by stimulating chondrocytes (or fibrochondrocytes) embedded in the tissue to synthesize cartilage matrix. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent. The subject method can further be used to prevent the spread of mineralisation into fibrous tissue.

In an illustrative embodiment, the subject method is used to treat cartilage of a diarthroidal joint, such as knee, an ankle, an elbow, a hip, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of an ECM-altering agent into the joint with, for instance, an arthroscopic needle, can be used to treat the afflicted cartilage. In some instances, the injected agent can be in the form of a hydrogel or other slow release vehicle described above in order to permit a more extended and regular contact of the agent with the treated tissue.

Moreover, as described above, the ECM-altering enzyme can be formulated and delivered to a specific location. For instance, slow release polymers can be localized to a particular treatment area of a mensical disc. To illustrate, degenerative changes are prominent in the triangular cartilage disc of the wrist joint of elderly people. The degeneration is more frequent and advanced on the ulnar side of the disc, perhaps because the biomechanical forces are more intense on that side. The degeneration affects the avascular portions of the disc but not the vascularized edges. Thus, an ECM-altering enzyme can be localized to the center of the ulnar face of the disc to enhance reparative process in that portion of the disc without substantially altering the integrity of the rest of the disc.

In another illustrated embodiment, the subject method can be used to treat cartilage of the costal sternum. After open chest surgery, such treatment can be opportunely employed in speeding reattachment of severed ribs to the sternum, as well as to decrease the amount of fibrotic tissue generated during healing.

In yet another embodiment of the subject method, an ECM-altering agent is contacted with cartilage of the pubic symphysis to enhance reattachment of the hip bones. For example, such treatments can be utilized in a female patient after delivery of a baby in order to mediate healing of the pubic symphysis which has undergone an intracartilaginous fissure from the degeneration of hyaline cartilage before and during labor.

In still a further embodiment, the subject method is applied to prevent replacement of hyaline cartilage after injury or other degenerative disorders, by other kinds of connective tissue such as fibroses or fibrous cartilage, as well as to prevent ossification of cartilaginous tissues. For example, the present invention can be used in the treatment of disorders in which cartilage is replaced by bone Treatment of this tissue by the subject method can inhibit the spread of mineralisation into the cartilage tissue by stimulating production of new cartilage matrix which turns over or otherwise replaces cartilage which is undergoing osteogenic processes.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, because the implant lacks of the ability to appropriately respond. For instance, when meniscal cartilage is used to repair anterior cruciate ligaments, the tissue undergoes a metaplasia to pure fibrous tissue.

By promoting chondrogenesis, the present invention can be used to particularly addresses this problem, by causing the implanted cells to become more adaptive to the new environment and effectively resemble hypertrophic chondrocytes of an earlier developmental stage of the tissue. Thus, the action of chondrogensis in the implanted tissue, as provided by the subject method, and the mechanical forces on the actively remodeling tissue will synergize to produce an improved implant more suitable for the new function to which it is to be put.

In similar fashion, the subject method can be applied to enhance remodeling of ligaments or tendons that are surgically shortened. For example, the present invention can be used to treat temperomandibular joint dysfunction (TMJ) either in regenerating the disc (as described for other joints above) or in the repair or replacement of the ligamental tissue which articulates the disc with the surrounding skeletal bones to correctly position the disc on the head of the condyle. For instance, in certain forms of TMJ, the ligaments have been stretched such that the interarticular disc is positioned either anterior or posterior to the condyle head. Surgical procedures to shorten the ligaments have been used to correct this deformity. The subject method can be used in the treatment of the shortened ligament to provide an improved ligament having zonal patterning that has advantageously been developed by the active remodeling of the "new" ligament by chondrocyte activation. Moreover, the present invention can prevent the occurrence of fibrotic tissue in the shortened ligament.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with an ECM-altering activity during the culturing process, such as a chondroitinase, in order to further stimulate cartilage matrix production within the implant. In such as manner, the cultured cells continue to maintain a phenotype typical of a chondrogenic cell (i.e. hypertrophic), rather than mature chondrocytes, and hence continue the population of the matrix and production of cartilage tissue.

In another embodiment, the implanted device is treated with an ECM-altering activity in order to actively remodel the implanted matrix so as to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the present invention is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

The invention now being generally described, it will be more readily understood by reference to the following examples which are included merely for purposes of illustration of certain aspects and embodiments of the present invention, and are not intended to limit the invention.

EXAMPLE 1

This experiment was designed to determine the cytotoxicity of chondroitinase for bovine articular cartilage cells in sub-confluent primary culture. These cells were preincubated for 48 hours in standard wells in Ham's F-12 medium with and without 10% fetal bovine serum. The medium was removed and replaced with the same medium containing no chondroitinase ABC (control) or from 0.5–00005 units/ml. of chondroitinase ABC. The cells were incubated for 48 hours, fixed, and counted. The results of this experiment are presented in Table One.

TABLE 1

Cytoxicity of Chondroitinase ABC

|  | Chondroitinase ABC (units/ml) | Cells (number/well) |
|---|---|---|
| Serum (−) | 0 | 70.3 ± 3.3 |
|  | 0.00005 | 63.3 ± 3.9 |
|  | 0.0005 | 53.0 ± 5.1 |
|  | 0.005 | 43.3 ± 4.8 |
|  | 0.05 | 41.0 ± 3.6 |
|  | 0.5 | 48.7 ± 7.8 |
| Serum (+) | 0 | 96.3 ± 21.7 |
|  | 0.00005 | 108.7 ± 11.7 |
|  | 0.0005 | 87.0 ± 4.5 |
|  | 0.005 | 94.3 ± 9.0 |
|  | 0.05 | 91.7 ± 9.6 |
|  | 0.5 | 100.3 ± 10.3 |

The cell number within each major group (serum+and serum−) are not significantly different. Two main conclusions are drawn from these data: 1) The concentrations of chondroitinase ABC added to these cells are not toxic; the cells within each group survived under all conditions, and 2) The presence of serum is not deleterious to the experimental conditions.

EXAMPLE 2

Further experiments were designed to examine the effect of chondroitinase on the activities of chondrocytes. In these experiments the production of chondroitin-4-sulfate was used as a marker of cartilage proteoglycan production. This form of chondroitin sulfate is the principal form produced by active cartilage-producing chondrocytes, and is the principal form found in the proteoglycan associated with cartilage. As a control the production of chondroitin-6-sulfate was evaluated. This form of chondroitin is found as the principal form in fibroblasts and in fibroblast-like chondrocyte revertents. The primary difference between the two parallel experiments was the age of the culture before exposure to chondroitinase. In one instance, the cells represented a primary culture while in the other the cells were put through 5 passages. In the latter, as a consequence of the multiple passages, a certain percentage of the chondroblasts revert to a fibroblast-like phenotype. That is, while still retaining some cartilage ECM capacity, they also behave like fibroblast. For example, these cells begin synthesizing large quantities of chondroitin-6-sulfate containing proteoglycans.

Chondroitinase ABC was a derivative of the bacterium *Proteus vulgaris* obtained from one of two sources, Seikagaku America and Taiyo Fishery Co., Ltd. Anti proteoglycan specific for one of chondroitin-6-sulfate or chondroitin-4-sulfate were obtained from ICN. These mouse monoclonal antibodies are able to recognize epitopes of the core protein of cartilage proteoglycan normally containing one of either chondroitin-6-sulfate or 4-sulfate, respectively. Anti-mouse IgG goat-biotin was also purchased from ICN. Streptavidin-Alkaline phosphatase was purchased from GIBCO. p-Nitrophenylphosphate was used as the substrate for the enzyme reaction. The washing and sample buffer was a mixture of PBS and 0.05% Tween 20.

Chondrocytes from bovine articular cartilage were removed from the extracellular matrix (ECM) by dissolving the ECM with collagenase. The were placed in Ham's medium containing fetal bovine serum (see Example 1) and cultured in 100 mm petri dishes for either three weeks, with three passages into fresh medium (set #1) or for five weeks and five passages (set #2).

At the end of the three week or five week period, aliquots from each culture of $3 \times 10^4$ cells were inoculated into individual wells of a standard 96-well plate. After three days, the cultures were rinsed gently with physiological buffered saline (PBS), and incubated with from 0–0.5 units per ml. of chondroitinase ABC for 20 minutes. After 20 minutes, the medium containing chondroitinase was replaced with normal medium. Each culture was then maintained in the regular medium for three days.

To obtain cell counts, wells and the number of cells in individual wells determined after removing the cells from the wells by trypsinization. The remaining cultures (those to be used for the Elisa experiments) were first washed with PBS and then fixed with 2% paraformaldehyde in cacodylate buffer. The specimens were stored at 4° C. until ready for the Elisa experiments.

In order to challenge the monoclonal antibodies after fixation, and to determine if the cells were damaged by the live incubation with chondroitin sulfate, the cultures were treated for one (1) hour at 37° C. with 0.05 units/ml albumin (BSA), pH 8.0. (BSA was added as a protease inhibitor to prevent the disruption of the core protein).

The first antibody (e.g. directed to the proteoglycan) was added to the plates and incubated for eighteen hours at 4° C. After incubation, the wells were washed with rinsing buffer three times before the addition of the second antibody. The second antibody (Goat anti-mouse IgG-biotin conjugate) was added to the wells, and the cells were incubated for two hours at room temperature. The wells were then washed with rinsing buffer three times before the addition of the phosphatase-streptavidin conjugate, and incubated for two hours. The plates were then washed three times with rinsing buffer before enhancement. For substrate level enhancement the plates were treated with 0.1% para-nitrophenylphosphate in buffer containing 22 mmol/l sodium carbonate, 28 mmol/l sodium bicarbonate, and 1 mmol/l magnesium chloride (pH 9.8) for 30 minutes. After enhancement the optical density at 405 nm was measured for each of the wells.

TABLE 2

The Effect of Chondroitinase on Chondrocytes

| | Chondroitinase ABC (units/ml.) | 0 | 0.005 | 0.01 | 0.05 | 0.5 |
|---|---|---|---|---|---|---|
| Ch-6-S | Mean | 0.648 | 0.564 | 0.640 | 0.631 | 0.658 |
| | SD | 0.044 | 0.062 | 0.018 | 0.016 | 0.013 |
| | % deviation from 0 conc. | — | −12 | −1 | −3 | +2 |
| Ch-4-S | Mean | 0.248 | 0.247 | 0.268 | 0.297 | 0.327 |
| | SD | 0.007 | 0.013 | 0.018 | 0.018 | |
| | % deviation from 0 conc. | — | 0 | +8 | +20 | +32 |
| Cell Number × 10,000/ well | Mean | 2.93 | 3.34 | 2.81 | 2.75 | 2.89 |
| | SD | 0.16 | 0.59 | 0.12 | 0.27 | 0.18 |

Table 2 illustrates the results of the chondroitinase treatment of the set #1 cells. The data indicates that the production of proteoglycan comprising chondroitin-4-sulfate increases with increasing concentration of chondroitinase ABC. Conversely, the proteoglycan comprising chondroitin-6-sulfate was not significantly altered with chondroitin ABC treatment. This experiment demonstrates that chondrocytes are stimulated to produce new cartilage proteoglycan.

Table 3 illustrates the results of the experiment with the older chondrocyte primary culture (set #2). Additionally, there is a small increase in the amount of chondroitin-6-sulfate with increased doses of chondroitinase, presumably resulting from the activity of chondrocytes that have reverted to fibroblasts. There is a significant dose-dependent increase in the amount of chondroitin-4-sulfate being produced, confirming the results of Table 2 above that indicate the ability of chondroitinase to stimulate cartilage.

TABLE 3

The Effect of Chondroitinase on chondrocytes and presumptive fibroblast revertants.

| | Chondroitinase ABC (units/ml) | 0 | 0.005 | 0.01 | 0.05 | 0.1 | 0.5 |
|---|---|---|---|---|---|---|---|
| Ch-6-S | Mean | 1.467 | 1.486 | 1.539 | 1.567 | 1.657 | 1.602 |
| | SD | 0.024 | 0.024 | 0.016 | 0.025 | 0.036 | 0.028 |
| | % deviation from 0 conc. | — | 1 | 4.9 | 6.8 | 13 | 9.2 |
| Ch-4-S | Mean | 3.96 | 4.53 | 4.7 | 5.01 | 5.87 | 5.83 |
| | SD | 0.02 | 0.026 | 0.027 | 0.027 | 0.003 | 0.016 |
| | % deviation from 0 conc. | — | 4 | 18.6 | 26.5 | 48.2 | 47.2 |
| Cell Number × 10,000/well | Mean | 3.3 | 3.1 | 3.1 | 3.1 | 3.3 | 3.3 |
| | SD | .2 | .1 | .2 | .2 | .1 | .1 |

The cells used in this later set of experiments are, in fact, believed to be more analogous to the cartilage of the osteoarthritic condition, where more chondroitin-6-sulfate is produced than in normal tissue.

EXAMPLE 3

Figure 1:
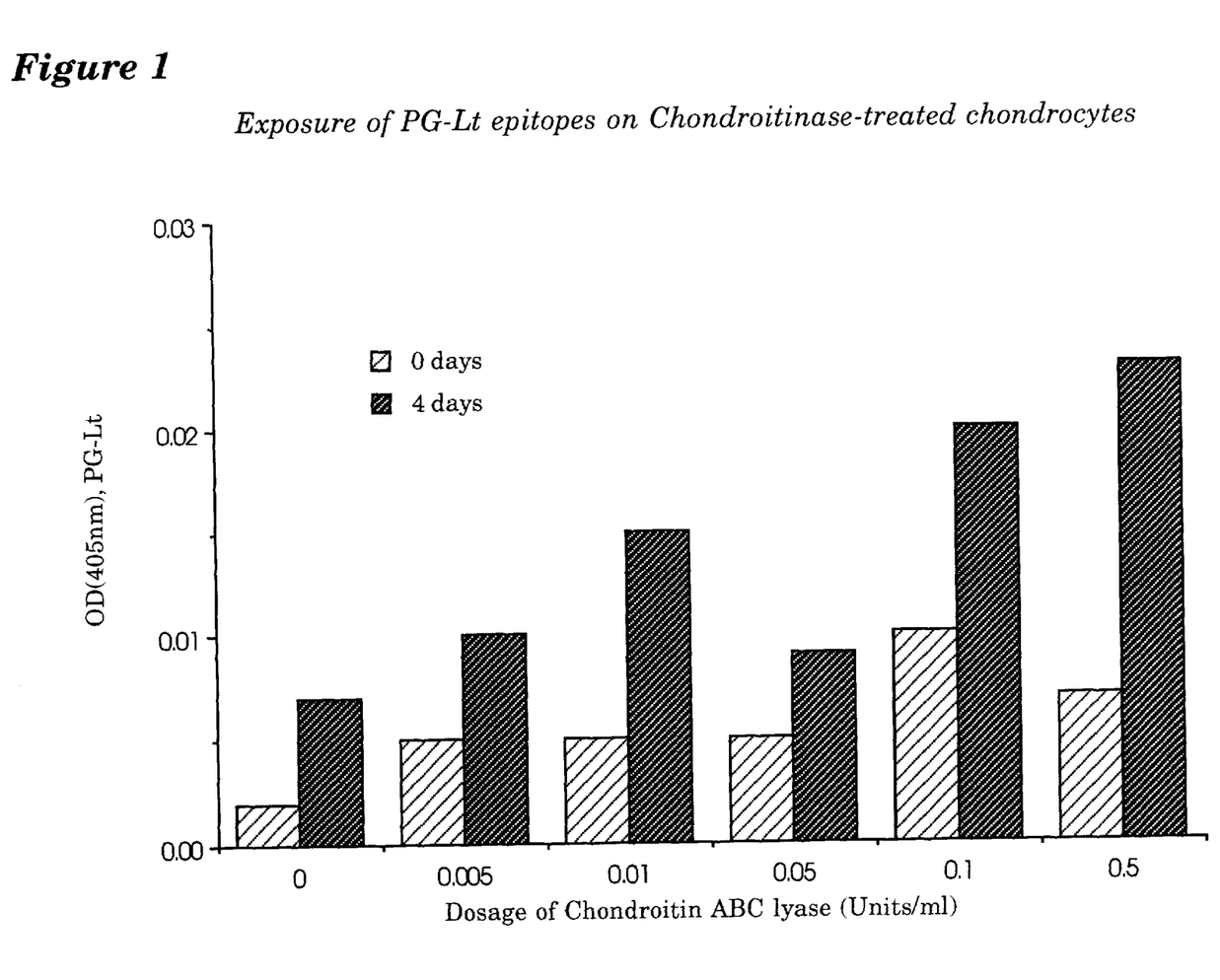
FIG. 1 illustrates the dose-dependent synthesis of aggrecan by chondrocytes treated with chondroitin ABC lyase. The binding of an anti-aggrecan antibody (PG-Lt) was measured immediately after chondroitinase treatment ("0 days") and 4 days subsequent. As described below, antibody binding was assessed by EIA techniques utilizing detection of substrate release (absorbance at 405 nm).

An anti-aggrecan antibody (PG-Lt), which specifically binds the core protein of aggrecan, was employed to measure the ability of chondroitinase-treated chondrocytes to synthesize aggrecan as part of the new cartilage matrix produced by the stimulated cells. The experiments were performed in a similar manner to those described in Example 2, with the exception of the second chondroitinase treatment immediately prior to antibody treatment. As FIG. 1 illustrates, the level of aggrecan expression after 4 days was correlated with the chondroitinase treatment in a dose-dependent manner.

All of the above-cited references and publications are hereby incorporated by reference.

EQUIVALENTS

Those skilled in the art will recognize, or be able to ascertain using no more than routine experimentation, numerous equivalents to the specific methods and reagents described herein. Such equivalents are considered to be within the scope of this invention and are covered by the following claims.

We claim:

1. An in vitro method for stimulating generation of a cartilage proteoglycan comprising treating chondrocytes with an enzymatic activity which alters a proteoglycan component of extracellular matrix of the chondrocytes to synthesize cartilage proteoglycan.

2. The method of claim 1, wherein the enzymatic activity comprises a proteoglycanase which depolymerizes a glycosaminoglycan chain of the proteoglycan component.

3. The method of claim 1, wherein the proteoglycanase is a chondroitin ABC lyase.

4. The method of claim 3, wherein the chondroitin ABC lyase is EC 4.2.2.4.

5. The method of claim 1, wherein the enzymatic activity comprises a protease which cleaves a peptide bond of a core polypeptide sequence of the proteoglycan component.

6. The method of claim 1, wherein the enzymatic activity does not substantially enzymatically alter any collagen matrix component of the chondrocyte.

7. The method of claim 1, wherein the chondrocytes are cartilage explants.

8. The method of claim 7, wherein in vitro culture of chondrocytes comprises a prosthetic device for implantation.

9. The method of claim 8, wherein the prosthetic device is an artificial meniscus.

10. The method of claim 8, wherein the prosthetic device is an artificial tendon.

11. The method of claim 8, wherein the prosthetic device is an artificial ligament.

12. The method of claim 1, wherein the proteoglycan component comprises aggrecan.

13. The method of claim 1, wherein the proteoglycan component comprises chondroitin-4-sulfate.

14. The method of claim 1, wherein the cartilage is of a diarthrodial joint.

15. The method of claim 1, wherein the diarthrodial joint is selected from a group consisting of a knee, an ankle, an elbow, a hip, a wrist, a shoulder, a knuckle of a finger, a knuckle of a toe, and a tempomandibular joint.

16. The method of claim 1, wherein the cartilage is articular cartilage.

17. The method of claim 1, wherein the cartilage is interarticular cartilage.

* * * * *